United States Patent

Borody

Patent Number: 5,273,032
Date of Patent: Dec. 28, 1993

[54] OXYGENATING ORAL MEDICAL APPLIANCE

[75] Inventor: Thomas J. Borody, Sydney, Australia

[73] Assignee: Gastro Services Pty Ltd., New S. Wales, Australia

[21] Appl. No.: 853,765

[22] PCT Filed: Nov. 27, 1990

[86] PCT No.: PCT/AU90/00569

§ 371 Date: May 29, 1992

§ 102(e) Date: May 29, 1992

[87] PCT Pub. No.: WO91/08012

PCT Pub. Date: Jun. 13, 1991

[30] Foreign Application Priority Data

Dec. 1, 1989 [AU] Australia ............... PJ 7664

[51] Int. Cl.$^5$ ........................................... A61M 16/00
[52] U.S. Cl. .................. 128/207.14; 128/207.18; 128/200.26; 128/200.24; 128/203.12; 128/204.18
[58] Field of Search ............ 128/4, 5, 6, 207.14, 128/204.18, 203.12, 911, 912, 200.24, 200.26, 207.18

[56] References Cited

U.S. PATENT DOCUMENTS

| 146,730 | 1/1874 | Vickers | 128/207.14 X |
|---|---|---|---|
| 2,127,215 | 8/1938 | Gwathmey | 128/207.14 |
| 2,705,959 | 4/1955 | Elmore | 128/207.14 |
| 3,756,244 | 9/1973 | Kinnear | 128/207.14 |
| 4,231,364 | 11/1980 | Speshyock | 128/206.15 |
| 4,270,531 | 6/1981 | Blachly | 128/207.14 |
| 4,881,542 | 11/1989 | Schmidt | 128/207.14 |

FOREIGN PATENT DOCUMENTS

| 0275105 | 7/1988 | European Pat. Off. | 128/200.24 |
|---|---|---|---|
| 3543931 | 6/1987 | Fed. Rep. of Germany . | |
| 3179009 | 12/1988 | Fed. Rep. of Germany . | |
| 1558171 | 12/1979 | United Kingdom . | |
| 2173105 | 10/1988 | United Kingdom . | |

*Primary Examiner*—Edgar S. Burr
*Assistant Examiner*—Eric P. Raciti
*Attorney, Agent, or Firm*—Bucknam and Archer

[57] ABSTRACT

An endoscopic mouth guard having a smoothly contoured, waisted tube merging into a peripheral flange at the front end of said tube, a manifold integral with the front face of said flange defining a closed ended, transverse distribution duct, and two open ended, upwardly directed branch ducts ending, in use, closely below the nostrils of a patient fitted with the guard, two further, open ended branch ducts extending rearwardly from said distributor duct into the bore of said tube, and a laterally and rearwardly directed tapered spigot on said manifold, defining an extension of said distributor duct, adapted to enter the bore of a gas supply tube. The finished guard is a single article of plastics material having a smooth hard surface.

6 Claims, 2 Drawing Sheets

OXYGENATING ORAL MEDICAL APPLIANCE

TECHNICAL FIELD

This invention relates to medical appliances, which are either used to keep a patient's mouth open for lengthy periods during some medical or surgical procedure, or, if used for some other purpose during such a procedure, necessarily have that effect. More particularly the invention relates to such appliances of an annular or tubular nature, intended to permit the patient to breathe through the mouth while fitted with the appliance.

BACKGROUND ART

One oral medical appliance which is typical of the kind to which the invention relates is the endoscopic mouth guard. This is essentially a short, right tube with somewhat flared or flanged ends, which is placed between the patient's lips and front teeth during gastroscopy to provide a safe and unobstructed passage for the endoscope. One such guard, characterised by its soft outer surface, is described and illustrated in U.S. Pat. No. 4,640,273 to F. R. Greene et al.

Another typical appliance of the kind in question is the so-called Guedel airway, which is used during recovery from anaesthesia, and comprises a curved tube adapted to be inserted partly into the mouth, through which the patient may breathe, and which is shaped to prevent the patient's tongue from falling into and blocking his or her windpipe.

It has been known for some time that patients who undergo endoscopic or other procedures requiring sedation frequently undergo hypoxia, that is to say an undesirable fall in the oxygen saturation level of the blood. The level of hypoxia may be minor and, although undesirable, deemed to be tolerable. On the other hand it may be quite profound. Indeed, in elderly patients or those with compromised circulatory or pulmonary systems, the hypoxia induced by sedation and the physical presence in the windpipe of an endoscope can precipitate cardiac or respiratory arrest. Likewise the blood oxygen level may fall unduly during recovery from anaesthesia.

Thus, even though oral medical appliances of the kind in question are normally annular or tubular so that the patient may breathe through the open mouth, there is sometimes a need to administer oxygen to a patient fitted with such an appliance.

Presently used apparatus for supplying oxygen to a patient to lift the blood oxygen level comprise face masks, which cover the mouth and nose, and nasal prongs. The use of a mask is often quite impracticable when, for example during gastroscopy, the procedure requiring use of the appliance also requires unhindered access to the oral cavity. Furthermore, most conscious patients, even if sedated, find nasal prongs uncomfortable or otherwise objectionable and their use sometimes causes internal bruising or abrasion.

Therefore, conventional means for administering oxygen to a patient fitted with an oral appliance are often unsatisfactory or inconvenient.

DISCLOSURE OF INVENTION

An object of the present invention is to overcome the above indicated disabilities of the prior art by very simple means.

The invention achieves that object by the provision in an oral appliance of the kind in question of unobtrusive duct means for directing at least one supplementary stream of gas into the patient's airway. In use, that gas is usually oxygen, but of course may be an oxygen rich, breathable gas mixture if need be. The supplementary stream may be directed by the appliance into the mouth or into or towards the nostrils, but, for preference there are a plurality of streams respectively directed into the mouth and towards both nostrils simultaneously.

Therefore, the invention consists in an oral medical appliance of the kind comprising an annular or tubular body adapted to be inserted into a patient's mouth and which then defines a passage extending through the appliance into the patient's oral cavity, characterised by supplementary gas delivery means integral with said appliance and comprising an inlet port adapted for connection to a gas supply tube, at least one outlet opening positioned such that, in use, gas issuing from that outlet opening is entrained with the air inhaled by the patient, and a duct system connecting said inlet port to said outlet opening or each of them.

BEST MODE OF CARRYING OUT THE INVENTION

Figure 1:
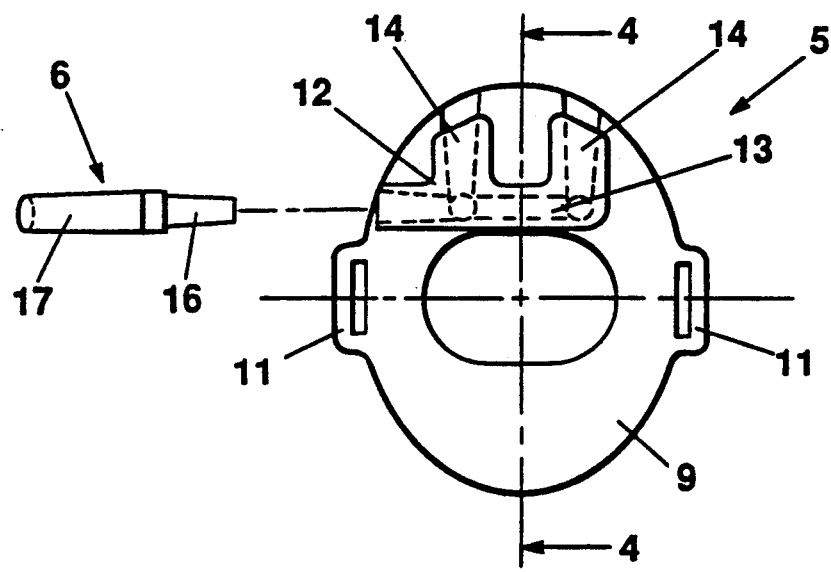
FIG. 1 is a front elevation of an endoscopic mouth guard according to one embodiment of the invention. This view is an "exploded" view in that the guard's two components, namely its annular body and inlet port structure respectively, are separated.
Figure 2:
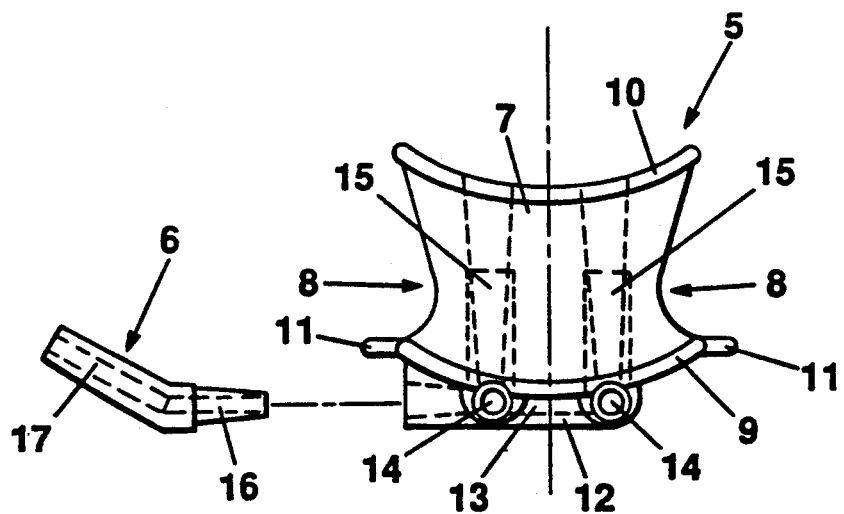
FIG. 2 is a similarly "exploded" plan view of the guard of FIG. 1, showing some hidden detail in broken line.
Figure 3:
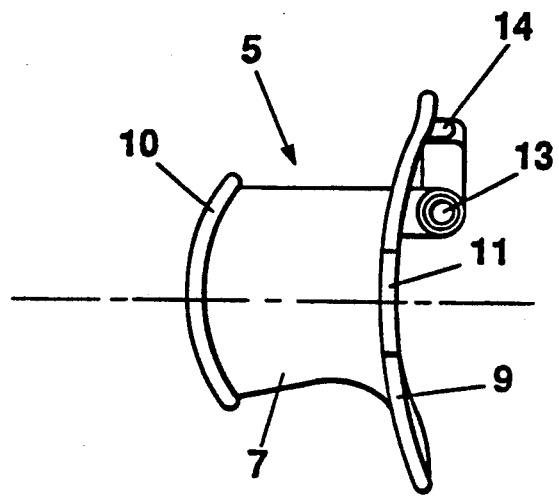
FIG. 3 is a side elevation of the guard of FIG. 1 with its inlet port structure omitted.
Figure 4:
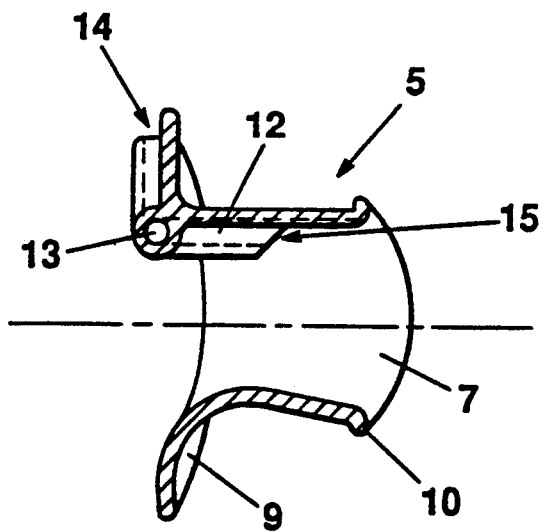
FIG. 4 is a sectional view taken on line 4—4 of FIG. 1.

As indicated above, the illustrated mouth guard comprises two components, an annular body 5 and an inlet port structure 6. Both components are preferably plastics mouldings. They may be of a highly polished durable material able to be heat sterilised a number of times, in which instance the appliance is intended for repeated use, or they may of a less expensive material and finish, in the instance of a disposable appliance intended to be used once only and then discarded.

The body 5 has rounded contours with no sharp edges. It comprises a short, rigid tube 7 which is waisted at 8 and merges at its outer end into a flared flange 9. It terminates at its inner end in a peripheral bead 10. It is of a size such that it may be inserted comfortably between the teeth of an adult patient with the flange 9 contacting and overlying the external lip area of the patient concerned, and the lips themselves making comfortable, more or less sealing, contact with the waisted portion of the tube 7. The guard as a whole may be secured in that position by a pliable, resilient, for example, elastomeric, band (not shown) extending from affixture eyes 11 around the back of the head of the patient.

Insofar as described above the guard's main body 5 is substantially conventional, but in accordance with the invention it incorporates supplementary gas delivery means comprising, in this instance, the inlet port structure 6 and a manifold structure 12 integral with the outer face of the flange 9 and the inner surface of the tube 7.

That manifold structure 12 defines a transverse distributor duct 13, two open ended upright branch ducts 14 extending from the distributor duct 13, and two horizontal branch ducts 15 also extending from the distributor duct 13. In use, the upright branch ducts 14 end close below and in substantial alignment with the nostrils of the patient, so that gas fed to them from the distributor duct 13 and issuing from them as the patient inhales is substantially entrained with any air breathed in through the nose. The rearwardly directed, horizontal branch ducts 15 end within the endoscope access passage defined by the tube 7, and thus any gas issuing from them will be entrained with any air breathed in through the mouth.

The inlet port structure 6 is essentially tubular and comprises a first tapered spigot 16 adapted to enter a correspondingly tapered mouth of the distributor duct 13 and a second tapered spigot 17 adapted to enter the bore of a conventional plastics oxygen supply tube. The taper and size of the spigot 17 is such that such a supply tube is frictionally retained on the spigot for leak-free communication therewith.

It will be seen that the spigots 16 and 17 meet at an included angle of about 150°. This enables the supply tube to extend away from the guard across and close to the patient's cheek so as not to interfere with the activities of the endoscopist.

The illustrated guard comprises two components purely for manufacturing convenience, as it would be difficult to mould the appliance in one piece. In the finished guard the inlet port structure 6 is permanently fixed to the main body 5 by virtue of the spigot 16 of the port structure 6 being welded or adhered permanently in the tapered mouth of duct 13.

In other embodiments of the invention the inlet port may be adapted for connection to the gas supply tube by means other than a tapered spigot. For example, it may be an enlarged end portion of the distributor duct functioning as a socket into which the end of the tube may be thrust.

The body of the illustrated embodiment is that of an endoscopic mouth guard but in other embodiments it may be that of a Guedel airway. As is well known such an airway comprises a short, straight, tubular mouthpiece with a front end peripheral flange and a long, rearwardly directed, arcuate, tubular tail adapted to overlie the patient's tongue and reaching to the top of the throat. Both the mouthpiece tube and the tail may be somewhat flattened and made of a softly resilient plastics material. In accordance with the invention such an appliance may have a manifold defining a distributor duct and two open ended branch ducts directed towards the patient's nostrils and one or more further open ended branch ducts extending through the front flange into the bore of the tail tube, in substantial accordance with the corresponding duct system of the illustrated mouthguard.

I claim:

1. An endoscopic mouth guard comprising a substantially tubular shaped body adapted to be inserted into a patient's mouth which leaves the patient's nose uncovered to permit natural breathing of ambient air and which defines a passage for an endoscope extending through the mouth guard into the patient's oral cavity, through which passage the patient may also breathe ambient air, and further including means for delivering supplementary gas integral with said mouth guard and comprising, an inlet port adapted for connection to a gas supply tube, at least one outlet opening further comprising means for entraining gas from said at least one outlet opening with at least some of the ambient air breathed in by the patient at a location exterior to said body, and a duct system connecting said inlet port to said at least one outlet opening.

2. The endoscopic mouth guard as defined in claim 1, which comprises a plurality of outlet openings, at least one of which is within said passage and two of which are respectively proximately below the patient's nostrils.

3. The endoscopic mouth guard as defined in claim 1, wherein said substantially tubular shaped body has a front peripheral flange adapted to overlie the patient's lips and said duct system is defined in part by a manifold integral with a front face of said flange.

4. The endoscopic mouth guard as defined in claim 1, wherein said inlet port comprises a tapered spigot adapted to enter the bore of a gas supply tube.

5. An endoscopic mouth guard comprising a waisted tube having a bore and a front end, a peripheral flange having a front face at said front end of said waisted tube, a manifold integral with the front face of said flange defining a closed ended, transverse distributor duct and two open ended, upwardly directed, branch ducts terminating proximately below the nostrils of a patient at least one further, open ended, branch duct extending rearwardly from said transverse duct into the bore of said tube, and connector means for connecting a gas supply tube to said distributor duct.

6. The endoscopic mouth guard as defined in claim 5, wherein said connector means comprise a tapered spigot extension of said distributor duct that is adapted to enter the bore of a gas supply tube.

* * * * *